US00PP14549P39

(12) United States Plant Patent
Whetman

(10) Patent No.: US PP14,549 P3
(45) Date of Patent: Feb. 17, 2004

(54) DIANTHUS PLANT NAMED 'NEON STAR'

(50) Latin Name: *Dianthus×hybrida*
Varietal Denomination: Neon Star

(76) Inventor: John Whetman, Houndspool Ashcombe Road, Dawlish, Devon, EX70 QP (GB)

( * ) Notice: Subject to any disclaimer, the term of this patent is extended or adjusted under 35 U.S.C. 154(b) by 0 days.

(21) Appl. No.: 10/071,058

(22) Filed: Feb. 7, 2002

(65) Prior Publication Data

US 2003/0150035 P1 Aug. 7, 2003

(51) Int. Cl.[7] ..... A01H 5/00
(52) U.S. Cl. ..... Plt./282

(58) Field of Search ..... Plt./282, 272, 278

(56) References Cited

PUBLICATIONS

The New Royal Horticultural Society Dictionary of Gardening, vol. 2, Editor–in–Chief Anthony Huxley, The Stockton Press, New York, 1992, pp 50–56.*

* cited by examiner

*Primary Examiner*—Anne Marie Grunberg

(57) ABSTRACT

A new cultivar of Dianthus named 'Neon Star' that is male sterile and characterized by intense magenta colored flowers, a compact habit, and a long flowering season. In combination these traits set 'Neon Star' apart from all other existing varieties of Dianthus known to the inventor.

2 Drawing Sheets

Genus: Dianthus.
Species: ×hybrida.
Denomination: Neon Star.

CROSS-REFERENCES TO RELATED APPLICATIONS

The application for this new invention is co-pending with one other application entitled Dianthus Plant Named 'Red Dwarf'. 'Red Dwarf' is derived from the same breeding program having the same inventor and filing date as the present application entitled Dianthus 'Neon Star'.

BACKGROUND OF THE INVENTION

The present invention relates to a new and distinct dwarf variety of Carnation that is grown for its compact habit and long flowering, fragrant, magenta blossoms. The new cultivar is known botanically as *Dianthus×hybrida* and will be referred to hereinafter by the cultivar name 'Neon Star'.

'Neon Star' is the product of a breeding program conducted by the inventor in a cultivated area of Houndspool, Dawlish, Devon, United Kingdom. The primary focus of the breeding program was to produce dwarf varieties with a wide range of bright colored perfume scented flowers with a long flowering season. The breeding program was established in 1969 in a cultivated area of Houndspool, Dawlish, Devon, United Kingdom. Open pollinated seedlings produced the female parent Dianthus 'Brehemen' (unpatented). The male parent is an unidentified Dianthus. The inventor bred 'Neon Star' in 1996 by induced hybridization.

'Neon Star' is a hybrid produced by induced hybridization and was selected by the inventor in 1997 for its intense magenta flowers, compact habit and long flowering season. The flower is generally male sterile but under exceptionally favorable environmental conditions it can produce anthers and pollen. 'Neon Star' is distinguishable from the female parent plant by flower color, a longer flowering season and a more compact habit. The flowers of the female parent 'Brehemen' exhibit more pink in their coloring (N74A).

In comparison, the plant most similar to 'Neon Star' is Dianthus 'Whatfield Magenta' (unpatented). 'Neon Star' differs from the comparison variety in its stronger growth, longer flowering season, and flower color. 'Neon Star' is 200% of the vigour of 'Whatfield Magenta'. The flowering period of 'Neon Star' is 25 weeks, whereas the flower period of 'Whatfield Magenta' is 5 weeks. Each individual flower of 'Neon Star' lasts approximately 5 days loner on the plant, than the individual flowers of 'Whatfield Magenta'.

Asexual reproduction of the new cultivar was first accomplished in 1997 by the inventor using softwood shoot cuttings in a cultivated area of Houndspool, Dawlish, Devon, United Kingdom. Since that time the characteristics of the new cultivar have been determined stable and are reproduced true to type in successive generations.

SUMMARY OF THE INVENTION

The following traits have been repeatedly observed and represent the characteristics of the new cultivar 'Neon Star'. These traits in combination distinguish this cultivar from all other commercial varieties known to the inventor. 'Neon Star' has not been tested under all possible conditions and phenotypic differences may be observed with variations in environmental, climatic and cultural conditions.

1. Dianthus 'Neon Star' flowers are generally male sterile, but under exceptionally favorable environmental conditions it can produce anthers and pollen.
2. Dianthus 'Neon Star' exhibits fragrant dark magenta colored flowers.
3. Dianthus 'Neon Star' exhibits a dwarf, compact cushion habit.
4. Dianthus 'Neon Star' reaches 13–16 cm. in height including the flower stalks and 25 cm. in width at maturity.

5. Dianthus 'Neon Star' is long flowering, blooming from April to October.
6. Dianthus 'Neon Star' is hardy to minus 15° Centigrade.

BRIEF DESCRIPTION OF THE DRAWINGS

The accompanying drawings illustrate the distinguishing traits of the new cultivar 'Neon Star' showing the colors as true as it is reasonably possible to obtain in colored reproductions of this type. Colors in the drawings may differ from the color values cited in the detailed botanical description, which more accurately describe the actual colors of the new variety 'Neon Star'.

The drawing on sheet 1 illustrates an entire mature plant.

The drawing on sheet 2 is a close-up view of the flower.

The flowers are an intensely saturated magenta color with a light-reflecting surface that sparkles. These qualities cannot be reproduced accurately by photography and are therefore not captured in these drawings. Both drawings are photographs of plants taken in Houndspool, Dawlish, Devon, United Kingdom in October 2001. No chemicals were used in treating the illustrated plants. The drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'Neon Star'. Data was collected from mature plants in the Houndspool, Dawlish, Devon, United Kingdom. The color determinations are in accordance with the 2001 Royal Horticultural Society Colour Chart of The Royal Horticultural Society, London, England, except where general color terms of ordinary dictionary significance are used.

Botanical classification: Dianthus 'Neon Star'.
Species: ×hybrida.
Common name: Carnation.
Commercial classification: Hardy perennial.
Use: Container and landscape plant.
Parentage: 'Neon Star' is a hybrid that resulted from the induced hybridization of the following plants.
*Female parent.*—Dianthus 'Brehemen' (unpatented).
*Male parent.*—Unidentified Dianthus.
Plant description:
*Bloom period.*—April to October.
*Plant habit.*—Dwarf, compact cushion habit.
*Height.*—13–16 cm. in height including the flower stalks.
*Width.*—25 cm. in width.
*Hardiness.*—Hardy to minus 15° Centigrade.
*Vigor.*—200% of Dianthus 'Whatfield Magenta'.
*Type.*—Perennial herb.
*Root system.*—Fine, fibrous, deep rooting system.
*Propagation.*—Propagation is accomplished with softwood shoot cuttings.
*Cultural requirements.*—Plant in full sun and retentive, well-aerated sandy loam with a pH of 6.5–7.0. This variety needs a high light intensity and long days.
*Diseases and pests.*—Susceptible to known Dianthus pests and disease but no other susceptibilities are known to the inventor.
*Time required to produce roots.*—2–3 weeks are needed to produce roots on initial cutting.
*Temperature recommended for cuttings to produce roots.*—The air temperature needed is 15–18° Centigrade and the base heat needed is 21° Centigrade.
*Crop time.*—5–7 months are needed for a rooted cutting to reach a finished one-gallon container size.
Stem:
*Shape.*—Cylindrical.
*Stem dimensions.*—6–7 cm. in length and 0.25 cm. in diameter.
*Stem surface.*—Glabrous and waxy.
*Stem color.*—189B.
*Branching.*—Numerous basal breaks.
*Internode length.*—4–5 cm. between nodes.
*Node color.*—160D.
*Node dimensions.*—0.50 cm. in diameter and 0.50 cm. in height.
Foliage:
*Type.*—Evergreen.
*Shape.*—Linear.
*Division.*—Simple.
*Apex.*—Acute.
*Base.*—Concave.
*Venation pattern.*—Parallel.
*Vein color* (*abaxial surface*).—137A.
*Vein color* (*adaxial surface*).—137A.
*Margins.*—Entire.
*Attachment.*—Sessile.
*Stipules.*—None.
*Arrangement.*—Opposite.
*Surface* (*adaxial and abaxial*).—Glabrous and waxy.
*Leaf dimensions.*—50 mm. in length and 4 mm. in width.
*Leaf color* (*adaxial and abaxial surfaces*).—137A.
*Fragrance.*—None.
Flowers:
*Sexuality.*—Generally the flowers are male sterile but under exceptionally favourably environmental conditions anthers and pollen can be produced.
*Type.*—Raceme.
*Persistent or self-cleaning.*—Persistent.
*Flower dimensions.*—20 mm. in height and 35 mm. in diameter.
*Flower shape.*—Disc shaped.
*Throat depth.*—15 mm. in depth.
*Aspect.*—Facing upward.
*Bud color.*—144C at base and 59C on upper end.
*Bud dimensions.*—18 mm. in length and 4 mm. in width.
*Bud shape.*—Tubular and pointed.
*Petals.*—5 in number.
*Petals fused or unfused.*—Unfused.
*Petal margin.*—Slightly toothed 1–2 mm. deep.
*Petal shape.*—80° segment with a strap forming the tube attached below the ovary.
*Petal color* (*adaxial surface*).—59A underlaid with 53B.
*Petal color* (*abaxial surface*).—53B.
*Petal surface.*—Glabrous.
*Calyx dimensions.*—4 mm. in width and 17 mm. in length.
*Calyx color.*—144C at base and 59C on upper end.
*Calyx surface.*—Glabrous.
*Epicalyx color.*—144C at base and 59C on upper end.
*Number of sepals.*—5 in number.
*Sepals fused or unfused.*—Fused.

*Sepal shape.*—Fused into a cylinder except for pointed apex.
*Sepal margins.*—Minutely toothed.
*Sepal apex.*—Acuminate.
*Peduncle dimensions.*—13–16 cm. in length and 2 mm. in diameter.
*Peduncle color.*—N138.
*Fragrance.*—Subtle clove scent.
*Lastingness of flowers.*—Individual flowers last approximately 10 days on the plant.

Reproductive organs:
*Stamens.*—10 in number.
*Stamen dimensions.*—18 mm. in length and 0.75 mm. in diameter.
*Stamen color.*—155A.
*Anther color.*—155A.
*Pollen color.*—155A.
*Amount of pollen.*—Large amount.
*Anther dimensions.*—3 mm. in length and 1 mm. in diameter.
*Pistil.*—2 but occasionally 3.
*Pistil color.*—The upper side is 64A and the lower side is 155A.
*Pistil dimensions.*—2 cm. in length and 1 mm. in diameter.
*Pistil shape.*—Fibril.
*Stigma.*—Two.
*Stigma color.*—The upper side is 64A and the lower side in 155A.
*Stigma dimensions.*—0.75 mm. in width and 2.5 mm. in length.
*Ovary position.*—Superior.
*Ovary color.*—144C.
*Ovary shape.*—Pointed cylinder.
*Ovary dimensions.*—8 mm. in height and 3 mm. in width.

*Seed production:*
*Seed number.*—1–10 seeds produced.
*Seed shape.*—Oval.
*Seed surface.*—Wrinkled surface.
*Seed color.*—202A.
*Seed dimensions.*—2 mm. in diameter and 3 mm. in length.
*Fruit shape.*—Capsule.
*Fruit size.*—9 mm. in height and 4 mm. in width.
*Fruit color.*—144D.

I claim:

1. A new and distinct cultivar of Dianthus plant named 'Neon Star' as described and illustrated herein.

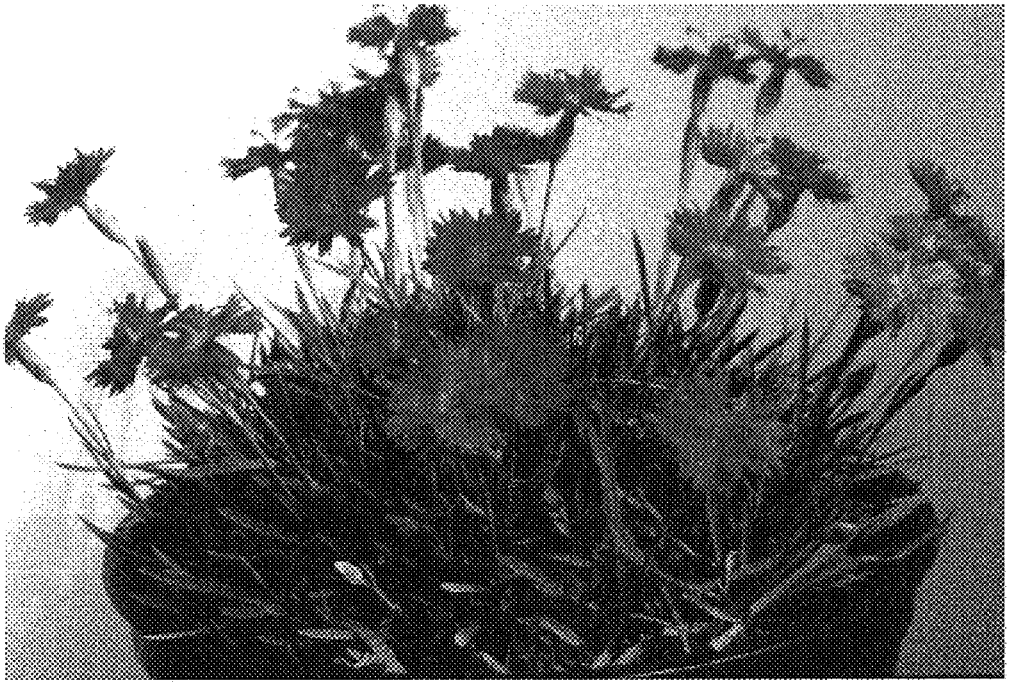

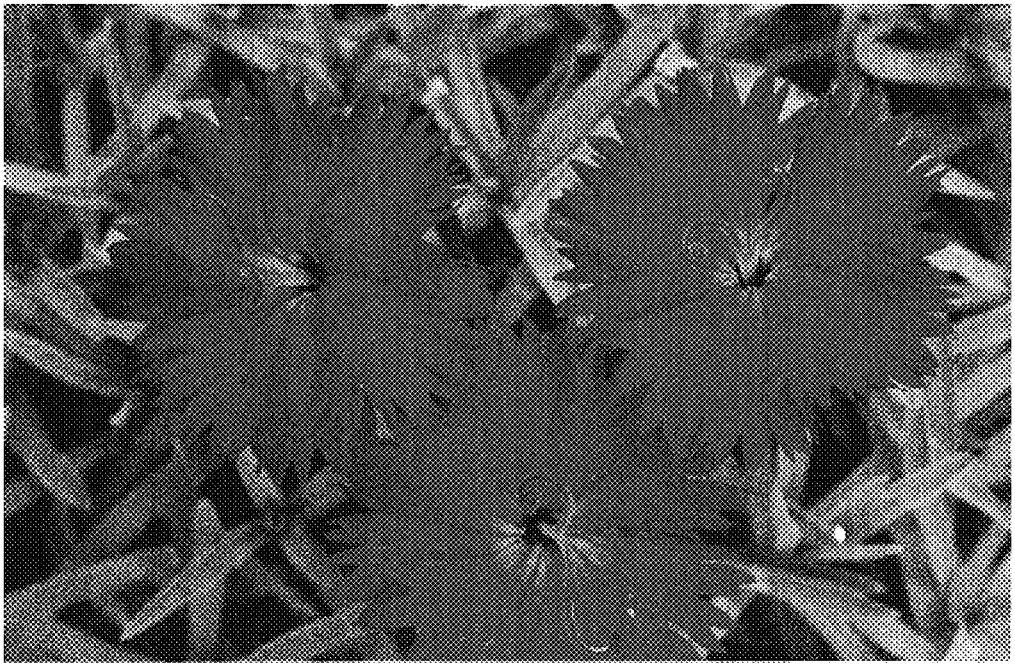

* * * * *